United States Patent [19]

Kim et al.

[11] 4,208,902
[45] Jun. 24, 1980

[54] GAS CONCENTRATION ANALYSIS METHOD AND SYSTEM

[75] Inventors: Bang M. Kim, Schenectady, N.Y.; John A. Quinn, Merion Station; David J. Graves, Devon, both of Pa.

[73] Assignee: Air Products and Chemicals, Inc., Allentown, Pa.

[21] Appl. No.: 971,613

[22] Filed: Dec. 20, 1978

[51] Int. Cl.² .............................................. G01N 7/10
[52] U.S. Cl. ........................................... 73/19; 55/158
[58] Field of Search .......................... 73/19, 23, 23.1; 55/158

[56] References Cited

U.S. PATENT DOCUMENTS

| 2,045,379 | 6/1936 | Bennett. | |
|---|---|---|---|
| 2,787,903 | 4/1957 | Beard | 73/23 |
| 2,866,329 | 12/1958 | Hanson | 73/23 |
| 3,367,850 | 2/1968 | Johnson. | |
| 3,518,982 | 7/1970 | Timmins et al. | 73/23 X |
| 3,545,931 | 12/1970 | McKinley, Jr. . | |
| 3,572,994 | 3/1971 | Hochstrasser . | |
| 3,658,479 | 4/1972 | Heijne et al. | 73/29 X |
| 3,866,460 | 2/1975 | Pearce, Jr. | 73/19 |
| 3,926,561 | 12/1975 | Lucero | 73/23.1 X |

OTHER PUBLICATIONS

Brantigan et al., *Nonthrombogenic Diffusion Membrane*, Journ. of App. Physio. 28(3), Mar. 1970, pp. 375–377.
Brantigan et al., *Teflon Membrane for Meas. of Blood.*, Journ. of App. Physio., 32(2), Feb. 1972, pp. 276–282.
Roberts et al., *Continuous Mass Spectrographic Meas.*, Med. & Bio. Eng., Jul. 1975, pp. 535–538.
Folkman et al., *Diffusion of Blood Gases*, Trans. Amer. Soc. Artif. Int. Organs., vol. XIII, 1967.

*Primary Examiner*—Gerald Goldberg
*Assistant Examiner*—Joseph W. Roskos
*Attorney, Agent, or Firm*—James C. Simmons; Barry Moyerman

[57] ABSTRACT

A method and system for analyzing gas concentration by measuring the steady state pressure in a dual membrane cell. A first membrane is exposed to a test gas and a second membrane to a reference gas where the first and second membranes have differing permeabilities. The test gas and the reference gas continuously counterdiffuse through the membranes and the steady state pressure in the intermembrane space is directly proportional to the gas concentration of the test gas component.

28 Claims, 11 Drawing Figures

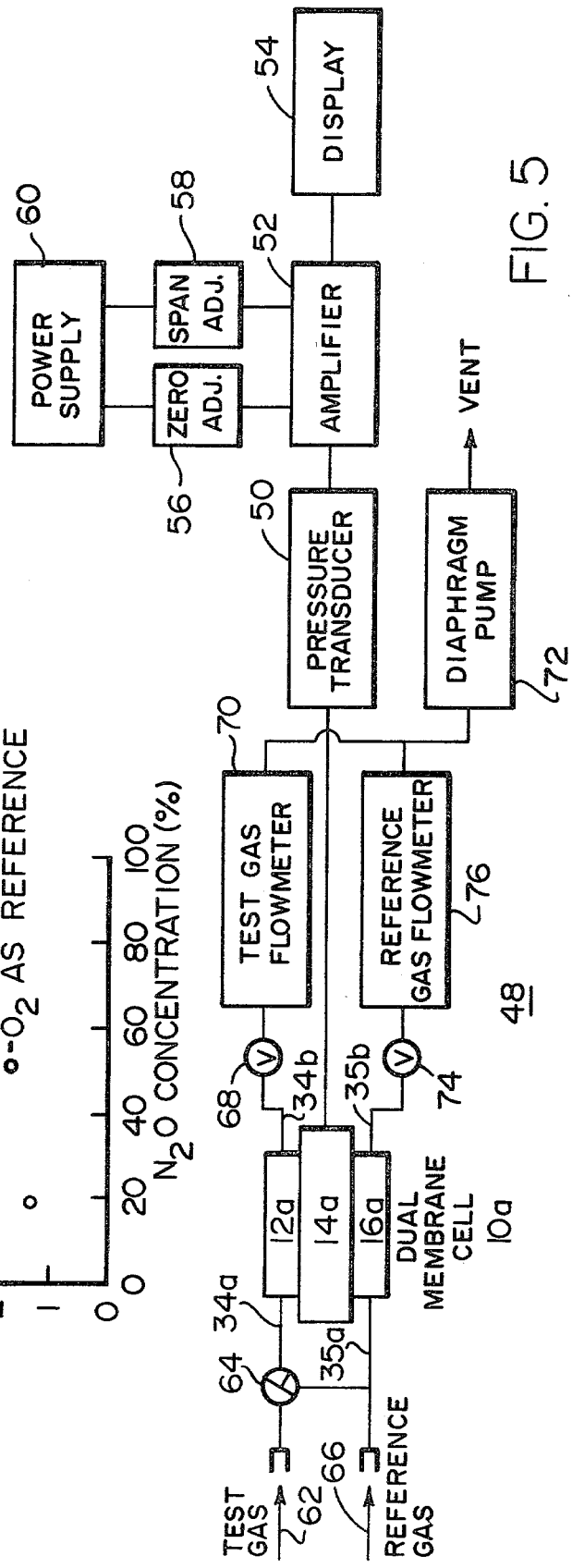

4,208,902

GAS CONCENTRATION ANALYSIS METHOD AND SYSTEM

BACKGROUND OF THE INVENTION

A. Field of the Invention

This invention relates to analysis of test gas mixtures using permselective membranes.

B. Prior Art

Gas analysis systems have been known which measure the concentration of a gas component in a test gas. For example, thermal conductivity gas analyzers have been used as binary gas analyzers. However, thermal conductivity analyzers have been limited due to their nonlinearity for various gas mixtures. In addition, these analyzers have required an external power supply to heat the detector element which heat has caused an explosion hazard in the measurement of explosive gases and has increased corrosion problems. Further, such heating element needs adjustment of its current depending upon the gases to be measured and may burn when the current is not adjusted correctly for a particular gas. Further, as a result of heating the heating element, thermionic noise has been generated which thereby limits the maximum sensitivity of the detector.

Permselective membranes have been known to provide various applications in gas analysis. For example, membranes have been used for sampling a specific gas for analysis with a gas analyzer. The gases have been collected by exposing selective membranes to gas or liquid streams and fed to a gas analyzer for concentration measurement. For example, $SO_2$, $NH_3$ $H_2O$ in the gas streams have been sampled by using Teflon and PVC membranes. These gas streams were then analyzed with flame photometers, katharometers and humidity sensors as described for example in U.S. Pat. Nos. 3,926,561; 3,545,931; and 3,367,850. It has further been known to measure the partial pressure of $CO_2$, $O_2$ and anesthetics in the blood and the $CO_2$ content of a solution by using silastic, Teflon and polyethylene membranes and using a mass spectrometer, an oxygen analyzer and other chemical analysis methods as disclosed, for example, in Brantigan, J. W., Gott, V. L., Vestal, M. L., Fergusson, G. J., and Johnston, W. H. "A nonthrombogenic diffusion membrane for continuous in vivo measurement of blood gases by mass spectrometry", *Journal of Applied Physiology*, Vol. 28, No. 3, March 1970, pp. 375-377; Brantigan, J. W., Gott, V. L., and Martz, M. N. "A Teflon membrane for measurement of blood and intramyocardial gas tensions by mass spectroscopy", *Journal of Applied Physiology*, Vol. 32, No. 2, February 1972, pp. 276-282; Roberts, M., Colton, III, E. T., Owens, G., Thomas, D. D., and Watkins, G. M. "Continuous mass spectrographic measurement of halothane partial pressure in blood", *Medical and Biological Engineering*, July 1975, pp. 535-538; and U.S. Pat. No. 3,572,994. In these methods, membranes have been used as an aid to a gas analyzer for the separation and concentration of specific gases for analysis with gas analyzers. Still other prior art has suggested the measurement of gas concentration by determining pressure response in a membrane-containing chamber as disclosed, for example, in Folkman, J., Winsey, H. S., and Cohen, B. "Diffusion of blood gases into an intravascular silicone rubber catheter: rapid measurement of anesthetic level, $pO_2$ and $pCO_2$ without blood sample", *Trans Amer. Soc. Artif. Int. Organs*, Vol. XIII, 1967, pp. 350-355; Folkman, J. Science, 157:203, 1967; and U.S. Pat. No. 3,518,982. In these systems, membranes had been used as a part of a gas analyzer. A test gas has been passed over a selective membrane which was attached to a constant volume chamber and the pressure response measured in the chamber. This procedure involved the following steps. The chamber was first filled with the reference gas, the test gas passed over the membrane with the initial pressure increase in the chamber then being measured. However, these prior methods were cumbersome and left much to be desired for a practical gas concentration analyzer.

Further references showing gas analysis systems and apparatus for diffusing gases are disclosed in the following U.S. Pat. Nos. 3,658,479; 2,866,329; 2,787,903; and 2,045,379.

Summary of the Invention

A method and system of measuring the concentration of at least one component of a test gas with respect to a reference gas in which the test gas is exposed to a first membrane and a reference gas is exposed to a second membrane. The first and second membranes have permeabilities so that the first membrane has a permeability ratio with respect to the test gas component over the reference gas which ratio is different from that of the second membrane permeability ratio with respect to the test gas component over the reference gas. The first and second membranes are separated from each other to form a measuring chamber between the membranes within which the steady state pressure is proportional to the concentration of the test gas component being measured.

BRIEF DESCRIPTION OF THE DRAWINGS

FIGS. 4A-B are views of a gas concentration measurement system using the dual membrane cell of FIG. 3 with a mercury manometer readout;

FIG. 5 is a schematic drawing of an electronic gas concentration measuring system using the dual membrane cell of FIG. 3;

FIGS. 6 and 7 are graphs useful in explaining the operation and comparing the operation of the electronic gas concentration measuring system of FIG. 5.

DETAILED DESCRIPTION

Figure 1:
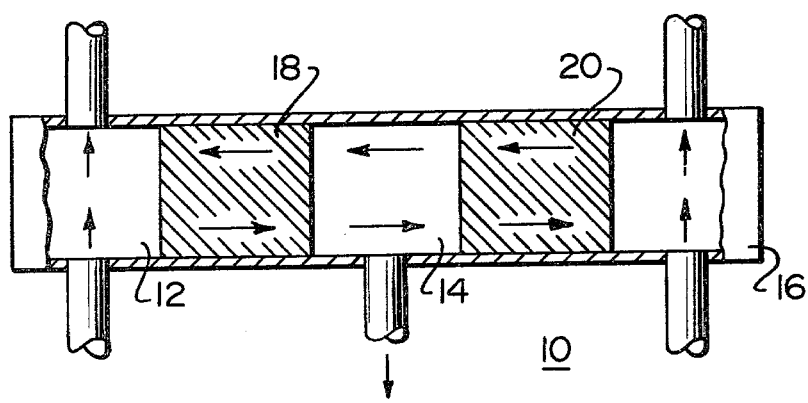
FIG. 1 is a top plane view partially broken away of a dual membrane cell (not in proportion) according to the invention.

Referring to FIG. 1, there is shown a three chamber dual membrane device 10 (drawn out of proportion for purposes of explanation) which measures the concentration of at least one component of a test gas with respect to a reference gas. The test gas component is defined as gas 1 and the reference gas is defined as gas 2. It will be understood that reference gas 2 may be a gas mixture. The three chambers comprise a test chamber 12, a middle measuring, chamber 14 and a reference chamber 16. These chambers are used to isolate the gas being measured from the environment as well as to expose the gases to test membrane 18 and reference membrane 20, respectively. Middle chamber 14 defines the intermembrane space and is isolated from the environment and from the test and reference chambers 12, 16 (and from the gases therein) by test and reference membranes 18,20, respectively.

Figure 2:
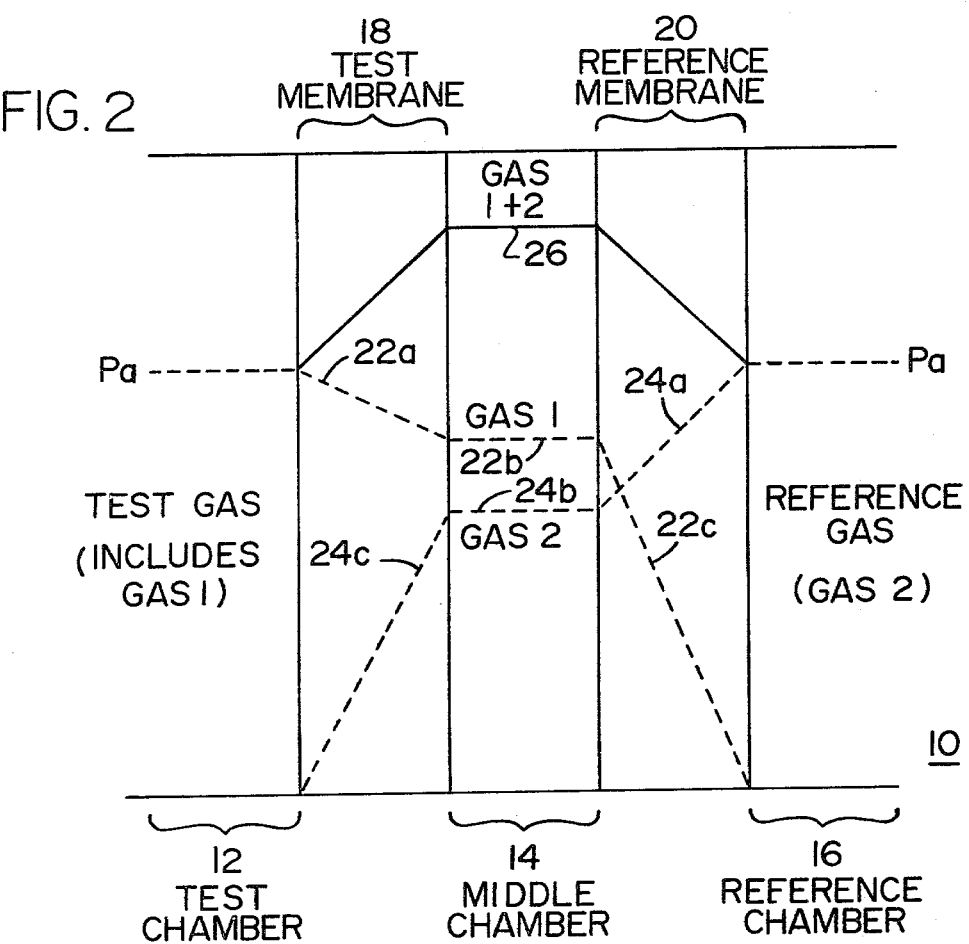
FIG. 2 is a schematic analysis of the dual membrane cell of FIG. 1.

FIG. 2 is a schematic analysis of dual membrane cell 10 of FIG. 1 and provides a time-flow representation of the diffusion of the test gas and the reference gas in a continuous counter diffusion flow mode through test and reference membranes 18,20. The flow of gas 1 through test chamber 12 exposes that gas to test membrane 18. Gas 1 may be represented as having a component under ambient pressure $P_a$ which diffuses through test membrane 18 with a concentration gradient indicated by the slope of dashed lines 22a. The gas 1 component (dashed lines 22b) then enters middle chamber 14 and has a partial pressure represented by the height of dashed lines 22b. The component then diffuses (dashed lines 22c) through reference membrane 20 at a concentration gradient higher than that with respect to lines 22a through membrane 18 and enters reference chamber 16 where it is carried away by the flow of the reference gas 2.

Reference gas (gas 2) under ambient pressure $P_a$ is exposed to reference membrane 20 in chamber 16 and diffuses through reference membrane 20 as shown by dashed lines 24a. Gas 2 then enters middle chamber 14 (dashed lines 24b) having a partial pressure represented by the height of dashed lines 24b. The gas 2 then diffuses through test membrane 18 as shown by dashed lines 24c and enters test chamber 12 where it is carried away with the flow of test gas.

It will be seen from FIGS. 1,2 that the slope of dashed lines 22a is different from the slope of dashed lines 22c and that the slope of dashed lines 24a is different from the slope of dashed lines 24c. This represents that the permeability of gas 1 through test membrane 18 is different from that of gas 1 through reference membrane 20, and that the permeability of gas 2 through reference membrane 20 is different from that of gas 2 through test membrane 18. Membranes 18,20 are selected of permeabilities so that membrane 18 has a permeability ratio with respect to gas 1 over gas 2 which ratio is different from that of membrane 20's permeability ratio with respect to gas 1 over gas 2.

As previously described, test gas 1 and reference gas 2 have partial pressure in middle chamber 14 as indicated by dashed lines 22b, 24b which when added together provide a total middle chamber pressure indicated by line 26. It will be understood that such middle chamber gas pressure is greater than ambient pressure $P_a$. As will later be described in detail with respect to theory, the summation of the partial pressures of the gases as seen in middle chamber 14 is linearly proportional to the concentration of gas 1. That is to say, the steady state pressure in chamber 14 is proportional to the concentration of gas 1 being measured.

In this manner, device 10 may be used to detect a gas component in a multicomponent gas stream and further provide a quantitative determination of that component's concentration. Different membrane materials may be selected for different gas components of interest and may further be selected to allow for pure or mixed reference gases by such selection of materials. Cells may be designed to cover a broad spectrum of gas streams and many components in a stream may be analyzed. The simplicity of cell 10 allows a reduction in total chamber volume so that there is a rapid response to concentration changes in the gas being measured. Additionally, the volumes of the cells may be made small enough to allow numerous cells to be incorporated in a single analyzer in order to provide a multicomponent analyzer which requires only small amounts of the test gas while providing a continuous concentration readout of each of the measured components.

Further as will later be described in detail, cell 10 may be constructed of relatively inexpensive materials while still providing a pressure indication which is linearly proportional to the concentration of the gas component being measured. Such a cell will have an overall accuracy and stability which is sufficient for the practical analysis of gaseous mixtures.

The counter diffusion of gases in a composite media has been described by Graves, D. J., Idicula, J., Lambertsen, C. J., and Quinn, J. A. "Bubble Formation in Physical and Biological Systems: A Manifestation of Counter-diffusion in Composite Media", *Science* 179, 1973, pp. 582–584. This article describes how a steady state pressure increase occurs between the media under a special condition. Also see Graves, D. J., Idicula, J., Lambertsen, C. J., and Quinn, J. A. "Bubble Formation Resulting from Counterdiffusion Supersaturation: A Possible Explanation for Isobaric Inert Gas 'Urticaria' and Vertigo", *Phys. Med. Biol.*, Vol. 18, No. 2, 1973, pp. 256–264.

With respect to dual membrane cell 10 shown in FIG. 1, the pressure increase in middle chamber 14 is produced when the gas 1 component has a higher permeability in membrane 18 (membrane t) than membrane 20 (membrane r) and gas 2 has a higher permeability in membrane r than membrane t. The total pressure in middle chamber 14 is the summation of each partial pressure and is larger than the pressure of the gases in chambers 12 and 16.

From the Science article, a generalized description of the pressure increase in cell 10 may be obtained by determining the partial pressure of each gas in middle chamber 14 and expressing the total pressure as a function of the pressures in chambers 12, 16. In cell 10, when n number of gases are present in test chamber 12, with partial pressure of $P_{i,t}$ and a gas of partial with $P_{j,r}$ is present in reference chamber 16, the total pressure in middle chamber 14 may be expressed by the following equation:

$$\overline{P} = \sum_{i=1}^{n} \left( \frac{K_{i,t} \Delta X_r}{K_{i,r} \Delta X_t + K_{i,t} \Delta X_r} \right) P_{i,t} + \frac{K_{j,r} \Delta X_t}{K_{j,r} \Delta X_t + K_{j,t} \Delta X_r} P_{j,r} \quad (1)$$

where
$\overline{P}$ = pressure in the middle chamber
$P_{m,k}$ = partial pressure of gas m in chamber k
$K_{m,k}$ = permeability of gas m in membrane k
$\Delta X_k$ = thickness of membrane which is exposed to chamber k where k is either test chamber or reference chamber
subscript i,j = gas i or j
   all gases present in test chamber—i
   all gases present in reference chamber—j
subscript t,r = membrane, test or reference This equation may be simplified for binary gas mixtures. If the mixture of gases 1 and 2 is present in test chamber 12 and gas 2 is in reference chamber 16 and if they are under equal ambient pressure, $p_a$, then the pressure in middle chamber 14 may be expressed by:

$$\bar{P} = \frac{K_{1,t}K_{2,r}\Delta X_r \Delta X_t - K_{1,r}K_{2,t}\Delta X_r \Delta X_t}{(K_{1,r}\Delta X_t + K_{1,t}\Delta X_r)(K_{2,r}\Delta X_t + K_{2,t}\Delta X_r)} P_{1,t} + P_a \quad (2)$$

where $P_{1,t}$ is the partial pressure of gas i in the test chamber.

Equation 2 shows that the pressure in middle chamber 14 is larger than the ambient pressure under the following conditions:

$$K_{1,t}K_{2,r}\Delta X_r \Delta X_t - K_{1,r}K_{2,t}\Delta X_r \Delta X_t > 0$$

or $$K_{1,t}/K_{2,t} > K_{1,r}/K_{2,r} \quad (3)$$

The pressure increase is directly proportional to the partial pressure of gas 1 as described by equation 2. Similar relationships may be obtained when a mixture of gases 1 and 2 are present in test chamber 12 and a gas 3 is in reference chamber 16. In this case, the pressure in middle chamber 14 may be expressed by:

$$\bar{P} = \frac{K_{1,t}K_{2,r}\Delta X_r \Delta X_t - K_{1,r}K_{2,t}\Delta X_r \Delta X_t}{(K_{1,r}\Delta X_t + K_{1,t}\Delta X_r)(K_{2,r}\Delta X_t + K_{2,t}\Delta X_r)} P_{1,t} + \quad (4)$$

$$\left(\frac{K_{2,t}\Delta X_r}{K_{2,r}\Delta X_t + K_{2,t}\Delta X_r} + \frac{K_{3,r}\Delta X_t}{K_{3,r}\Delta X_t + K_{3,t}\Delta X_r}\right) P_a$$

The pressure increase $\Delta P$ as defined by the following equation is proportional to $P_{1,t}$:

$$\Delta P \equiv \bar{P} - \left(\frac{K_{2,t}\Delta X_r}{K_{2,r}\Delta X_t + K_{2,t}\Delta X_r} + \frac{K_{3,r}\Delta X_t}{K_{3,r}\Delta X_t + K_{3,t}\Delta X_r}\right) P_a = \quad (5)$$

$$\frac{K_{1,t}K_{2,r}\Delta X_r \Delta X_t - K_{1,r}K_{2,t}\Delta X_r \Delta X_t}{(K_{1,r}\Delta X_t + K_{1,t}\Delta X_r)(K_{2,r}\Delta X_t + K_{2,t}\Delta X_r)} P_{1,t}$$

It will be understood that using the pressure response of cell 10, it is possible to analyze binary gas mixtures by measuring the pressure increase in middle chamber 14. The membranes which satisfy equation 3 are required to be chosen to obtain a positive pressure increase in this application.

A sample calculation has been made for analyzing a mixture of $CO_2$ and $O_2$ using a dual membrane cell 10 containing dimethyl silicone (DMS) as test memrane 18 and ethyl cellulose (ETCL) as a reference membrane 20. The permeabilities of each gas for these membranes are set forth as follows.

TABLE 1

| | | |
|---|---|---|
| $K_{CO_2,t}$ | = | $236 \times 10^{-9}$ cm³ (STP) cm/cm² · cm Hg · sec |
| $K_{CO_2,r}$ | = | $57.8 \times 10^{-9}$ cm³ (STP) cm/cm² · cm Hg · sec |
| $K_{O_2,t}$ | = | $58.7 \times 10^{-9}$ cm³ (STP) cm/cm² · cm Hg · sec |
| $K_{O_2,r}$ | = | $41.6 \times 10^{-9}$ cm³ (STP) cm/cm² · cm Hg · sec |

Since these permeability values satisfy equation 3, a steady state pressure increase occurs in middle chamber 14. It may be shown from a theoretical plot of pressure increase versus $CO_2$ concentration that a pressure increase is a function of the thickness ratio of the two membranes 18, 20 and the pressure increase is proportional to the $CO_2$ concentration.

There has now been described the steady state response of cell 10 and the following is a theoretical explanation of transient response. As an understanding of the shape of the transient signal and the parameters determining the response time are important herein. For dual membrane cell 10, the initial partial pressure of gases in each chamber are:

$$\begin{aligned} P_{1,t} &= P_1°,t \\ P_{2,r} &= P_2°,r \\ \bar{P}_1 &= \bar{P}_1° \\ \text{and} \quad \bar{P}_2 &= \bar{P}_2° \end{aligned} \quad (6)$$

When test and reference chambers 12 and 16 are flushed with gas 1 and gas 2 having partial pressures of $P_{1,t}$ and $P_{2,r}$, the transient pressure response in middle chamber 14 may be derived in the following manner. The material balance of gas i (the generalized case) for middle chamber 14 leads to $$\frac{d N_{i,m}}{dt} = \frac{P}{RT_o}\left[\frac{K_{i,t}A}{\Delta X_t}(P_{i,t} - P_{i,m}) - \frac{K_{i,r}A}{\Delta X_r}(P_{i,m} - P_{i,r})\right] \quad (7)$$

For an ideal gas $$\frac{d N_{i,m}}{dt} = \frac{V}{RT}\frac{d P_{i,m}}{dt} \quad (8)$$

Substituting equation 7 with equation 8 leads to $$\frac{d P_{i,m}}{dt} = \frac{R_o AT}{V}\left[\frac{K_{i,t}}{\Delta X_t}(P_{i,t} - P_{i,m}) - \frac{K_{i,r}}{\Delta X_r}(P_{i,m} - P_{i,r})\right] \quad (9)$$

where
A = area of the membrane
$N_{i,m}$ = moles of gas i in the middle chamber 14
$P_o$ = 76 mm Hg
R = gas constant
$R_o = P_o/T_o$
t = time
$T_o = 273°$ K
T = temperature of middle chamber 14
V = volume of the middle chamber 14

Integration of equation 9 leads to the following:

$$\bar{P} = P_{i,m} + P_{j,m} = \quad (10)$$

$$\frac{1}{E}\left\{B - (B° - EP_1°)\exp\left(\frac{-AERTt}{V\Delta X_r \Delta X_t}\right)\right\} +$$

$$\frac{1}{G}\left\{F - (F° - GP_2°)\exp\left(\frac{-AERTt}{V\Delta X_r \Delta X_t}\right)\right\}$$

where
$B = K_{i,t}\Delta X_r P_{i,t} + K_{i,r}\Delta X_t P_{i,r}$
$B° = K_{i,t}\Delta X_r P_{i,t}° + K_{i,r}\Delta X_t P_{i,r}°$
$E = K_{i,t}\Delta X_r + K_{i,r}\Delta X_t$ $$F = K_{2,r}\Delta X_t P_{2,r} + K_{2,t}\Delta X_r P_{2,t}$$
$$F^o = K_{2,r}\Delta X_t P_{2,r}{}^o + K_{2,t}\Delta X_r P_{2,t}{}^o$$
$$G = K_{2,r}\Delta X_t + K_{2,t}\Delta X_r$$

The first term of the foregoing equation is the transient response of gas 1 in middle chamber 14 and the second term is that of gas 2 in the middle chamber. The parameters of the exponential term define the factors determining the time to reach steady state. For each response, the response time will be short when the area of the membrane set forth as "A" in equation 10 and the permeability of the membrane "K" in the equation are large and the thickness of membrane "$\Delta X$" and the volume of the middle chamber "V" become small.

It will be understood that the characteristic of the transient response may be better explained by plotting the pressure response. A digital computer has been used for computing equation 10 for various values of the parameters and plotting the resultant responses.

Figure 3:
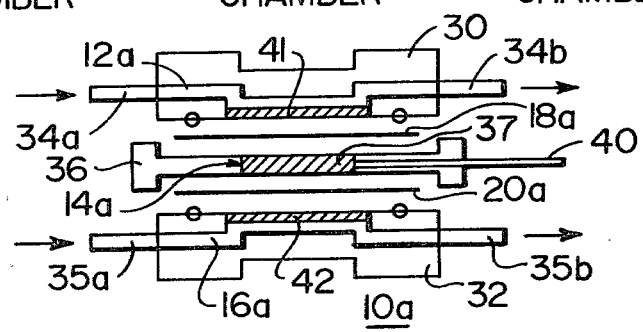
FIG. 3 is an exploded side view of an actual construction of a dual membrane cell shown representatively in FIG. 1.

In a computer simulated test run to demonstrate transient response, a dual membrane cell 10 used DMS as a test membrane 18a and ETCL as a reference membrane 20a in cell 10a, FIG. 3. Initially, helium at one atmosphere was flushed through both chambers 12a, and 16a. At t=0, $CO_2$ at one atmosphere was flushed through test chamber 12a instead of the helium flow. The parameter values used in the simulation were $$\overline{P}_1{}^o = P_{1,r} = P_{2,t} = 0.0 \text{ATM}.$$

$$\overline{P}_2{}^o = P_{1,t} = P_{2,r} = 1.0 \text{ATM} \qquad (11)$$

Figure 8:
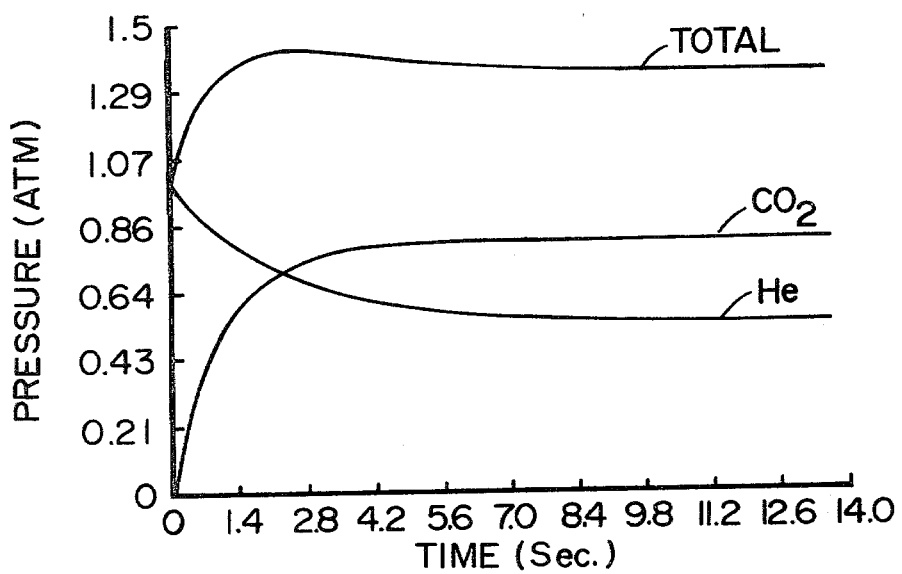

$K_{1,t} = 236 \times 10^{-9}$ cm$^3$(STP)· cm/cm$^2$· cm Hg·sec
$K_{1,r} = 57.8 \times 10^{-9}$ cm$^3$(STP)· cm/cm$^2$· cm Hg ·sec
$K_{2,t} = 64.4 \times 10^{-9}$ cm$^3$(STP)· cm/cm$^2$· cm Hg·sec
$K_{2,r} = 74.1 \times 10^{-9}$ cm$^3$(STP)· cm/cm$^2$· cm Hg·sec
$T = 293°$ K.
A, V, $\Delta X_t$, $\Delta X_r$ as specified on each plot
$\overline{P}_1{}^o$ = initial partial pressure of gas 1 in middle chamber
$\overline{P}_2{}^o$ = initial pressure of gas 2 in middle chamber FIG. 8 shows the response of the partial pressure of $CO_2$ and He in middle chamber 14. In the transient state, the rate of $CO_2$ diffusing into the middle chamber is faster than the rate of He diffusing out. This results in overshoot in the total pressure response. From FIG. 8, it may be seen that at the steady state, the total pressure (the summation of the two partial pressures) becomes higher than the initial pressure.

Figure 9:
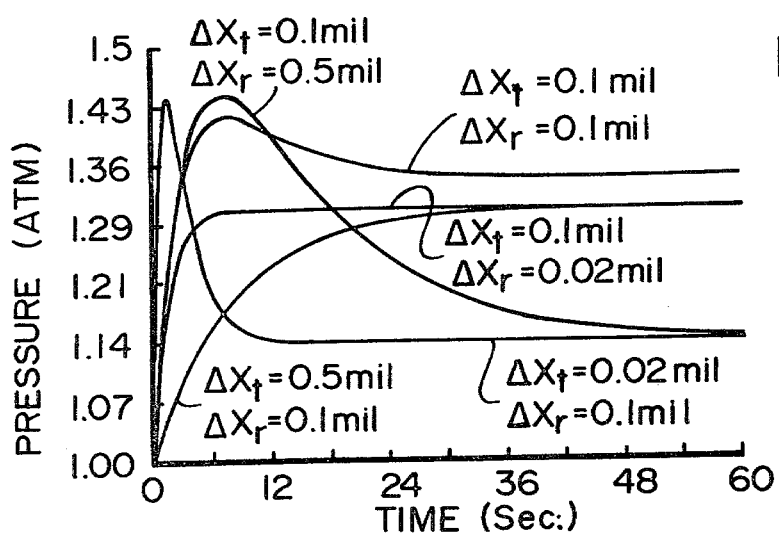

In FIG. 9, there is shown the response of the total pressure for various thickness of membrane. For example, when the thickness of ETCL is five times larger than DMS, the response in FIG. 9 shows a large overshoot. This overshoot decreases as the thickness of the DMS increases. When the thickness of the DMS is five times larger than that of the ETCL, no overshoot may be seen. It will be understood that overshoot is not desirable in the response of a concentration measurement system using cell 10. FIG. 9 further shows that the steady state pressure increases the same for the same membrane thickness ratio. It also demonstrates that smaller membrane thickness results in fast response time.

Figure 10:
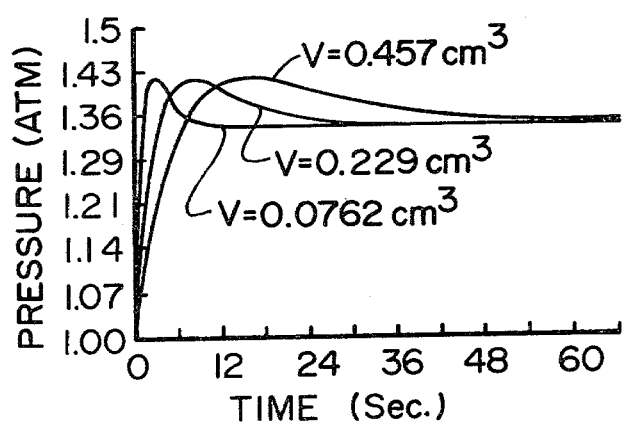
FIGS. 8-10 are graphs helpful in showing the response of the dual membrane cell of FIG. 3.

The response for various volumes in middle chamber 14 is shown in FIG. 10. A fast response time may be seen when there is a small volume in middle chamber 14. It will be understood by those skilled in the art that the desired response for gas analysis is a fast response time, a large pressure increase and no overshoot.

Cell 10 of FIGS. 1 and 2 in one form is shown in detail in FIG. 3 as dual membrane cell 10a. Cell 10a comprises a test membrane 18a, a reference membrane 20a, a test chamber 12a and a reference chamber 16a. In order to form chamber 12a, a brass housing 30 is hollowed out. Similarly, a housing 32, which also may be made of brass, is hollowed out to form chamber 16a. Pipes 34a,b form entrance and exit ports respectively for chamber 12a and pipes 35a,b form entrance and exit ports respectively for chamber 16a.

In order to provide a middle or measuring chamber 14a, a brass housing 36 has a hollowed center section within which is a porous stainless steel disc 37 which is used to reduce the volume of middle chamber 14a. A single tube 40 connects to middle chamber 14a to provide for coupling to a pressure readout. To support membranes 18a and 20a, porous stainless steel discs 41, 42 are respectively disposed between membrane 18a and chamber 12a and between membrane 20a and chamber 16a. It will be understood by those skilled in the art that the test and reference chambers are required to have substantially small volumes in order to minimize mixing volume.

While FIG. 3 has been shown for purposes of description in exploded form, it will be understood that the cell is held tightly together in conventional manner by external clamps and O-rings thereby to provide interchamber sealing. Direct contact seals may be used between metal and membrane and O-rings to provide sufficient pressure for such gas tight sealing.

The criteria for selecting membranes 18a, 20a are preferably to achieve a large pressure increase and a short response time in the manner previously described. In addition to DMS as a test membrane 18a, a silicone-polycarbonate copolymer (SPC) has also been used. Such a membrane is made by General Electric Co., Polymer XD-1. SPC has a slightly lower permeability than DMS and a thinner membrane may thus be prepared. In another example of membrane 18a, an effective thickness of 0.2–0.3 mil has been prepared by casting a solution containing 10% GE XD-1 in 1,2,3-trichloropropane on a glass plate.

With respect to the reference membrane 20a, the thickness required for ETCL has been found to be about 0.05 mil if there were to be no overshoot with respect to the thickness of the SPC membrane 18a. The thickness in such range was obtained by casting the ETCL solution on a water surface. The solution contained 8% ETCL in a solvent of a one to one ratio of 1,2,3-trichloropropane and toluene. This technique for preparing an ultrathin membrane on a water surface is described in WArd, III, W. J., Browall, W. R., and Salemme, R. M. "Ultrathin Silicone/Polycarbonate Membranes For Gas Separation Processes", *J. of Membr. Sci.* 1, 1976, pp 99–108. Both of such membranes 18a and 20a were supported by filter papers before placing them in cell 10a and the areas of each of the membranes was about 0.785 cm$^2$. A porous membrane, the permeability of which is determined by the Knudsen diffusion, may also be used as a reference membrane. Reference membrane 20a may be a Unipore membrane (made by Bio Rad Laboratories) with a pore size of 300 A and a thickness of 2 mil. Cell 10a with SPC/Porous membranes may be used to analyze most of the binary gas mixtures of industrial interest. The permeability data of these membranes show that any two combinations of the following gases, $N_2$, $O_2$, $CO_2$, $N_2O$, $NH_3$ and $SO_2$ may be analyzed.

Other examples of membranes 18, 18a and/or 20,20a which have operative characteristics which may be found to be suitable are:

polytetrafluoroethylene
cellulose acetate
polycarbonate
polyethylene
polypropylene
polyurethane
polyvinylchloride All of the foregoing membrane materials may be defined as polymeric membranes in which the solubility and the diffusivity determine the permeability. Further, glass, metallic or other porous membranes in which the Knudsen diffusion determines the permeability may be used which have the necessary properties.

Many different types of pressure measuring or indication systems may be coupled to tube 40 and thus to middle chamber 14, 14a in order to provide a measurement of the pressure in the middle chamber and thus a direct reading of the gas concentration of gas 1. For example, as shown in FIG. 5, an electronic system 48 is provided for dual membrane cell 10a, FIG. 3, in which tube 40 is coupled to a conventional pressure transducer 50. The signal change produced by transducer 50 is amplified by an amplifier 52 with the voltage output thereof indicated on a display 54. In manner well known to those skilled in the art, amplifier 52 is provided with a zero adjust circuit 56 and a span adjust circuit 58 both coupled between a power supply 60 and amplifier 52. Amplifier 52 may be a conventional instrument amplifier and transducer 50 may be a Setra Systems Model 390.

To provide for gas flow, a test gas is applied by way of a line 62 through a valve 64 to input port 34a of cell 10a. Reference gas 2 is applied by way of a line 66 to input port 35a. Output port 34b is coupled by way of a valve 68 through a test gas flowmeter 70 and a diaphragm pump 72 to vent. Similarly, output port 35b is coupled through a valve 74 and a flowmeter 76 through pump 72 to vent. Flowmeters 70 and 76 may be variable area flowmeters or rotameters.

In a typical example, flowmeters 70,76 may be set to 100 ml/min and the test gas may comprise a mixture of gas 1 and gas 2 while the reference gas is gas 2. Under these conditions, the following calibration method may be used. By suitable positioning of valve 64, 100% gas 2 from line 66 may be passed through both ports 34a and 35a and zero adjust 56 is set until display 54 reads zero. Thereafter, 100% gas 1 is applied to line 62 and valve 64 is adjusted so that 100% of gas 1 is only passed through inlet port 34a. Span control 58 is then adjusted until display 54 reads 100. The foregoing procedure is repated until there is no change in the zero and span adjustments. It will be understood that the binary gas mixture of gases 1 and 2 may be analyzed using a third gas 3 such as room air as a reference gas and applying a similar procedure.

Figure 7:
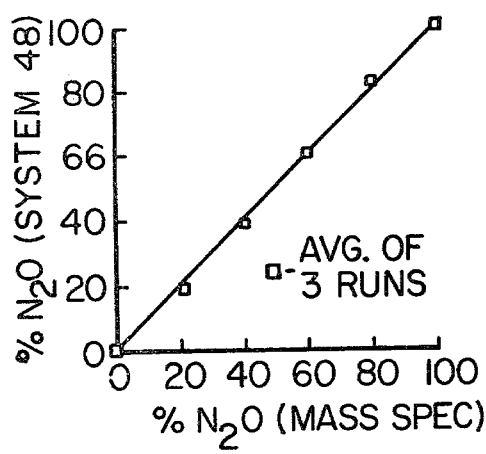

For system 48, a graph of pressure versus concentration is shown in FIG. 6 which shows the linearity of the response from zero to 100% concentration of N$_2$O. One of the curves shows air as a reference while the other curve shows oxygen as a reference. In a typical example we have fond this linearity to deviate less than ±1% over the full scale of display 54. Additionally, FIG. 7 shows a graph of per cent N$_2$O of system 48 compared with the results obtained from a conventional mass spectrometer. Thus, from this curve, it will be seen that the overall accuracy was found to deviate less than ±1% full scale of the display 54. Such system drifted less than 0.5% over an eight hour period. Further, we found that the humidity effect was less than 3% full scale for a 100% humidity at 25° C.

Instead of an electronic system 48 to measure concentration, the pressure from middle chamber 14a of cell 10a may be directly applied to a mercury reservoir as shown by a mercury manometer system 80 in FIG. 4. The advantage of system 80 is that it does not require an external source of energy. This is particularly important in certain applications, as for example, where the gas component being measured is an explosive gas and also in a portable instrument for field use.

As shown in FIG. 4, cell 10 is supported within a housing 81. Middle chamber 14a of the cell is coupled by way of a line 40a to a mercury reservoir 82 formed in housing 81. As known in the art, the pressure applied to a mercury reservoir is effective to raise or lower level 84 of the mercury in a cylinder or capillary tube 86 for a direct readout of the level of mercury. Since the pressure in chamber 14a is linearly proportional to the concentration of gas 1, the length of the mercury in column 86 indicates the concentration of gas 1.

It will be understood that level 84 may be calibrated by means of a conventional adjustable calibration chart 90 which is movable and then secured in position. By this system, manometer system 80 may provide a response time of 30 seconds, for example, and an overall accuracy of ±3% of the full scale value of the concentration known to be present in measuring nitrous oxide in a nitrous oxide-oxygen mixture. Pressure in chamber 14a may be directly read in the manner of manometer system 48 by other means such as a Bourdon tube and a bellows measurement device.

It will now be understood that by use of cells 10, 10a, a binary gas mixture may be analyzed providing the test gas has a component gas to be analyzed and a reference gas is provided. In this way, the dual membrane cell detects a component of a test gas as compared with the component concentration in the reference gas. A positive pressure is developed in the intermembrane space of middle chamber 14 which pressure is linearly proportional to the concentration of the component gas. It will be further understood that cell 10a provides membranes 18a, 20a and middle measuring chamber 14a which are of size sufficient to produce a measurement of concentration so that the response is independent of the rate of flow of the test gas and the reference gas over a predetermined range.

What is claimed is:

1. A method of measuring the concentration of at least one component of a test gas with respect to a reference gas comprising the steps of
   (a) exposing a first membrane to the test gas and a second membrane to the reference gas,
   (b) providing permeabilities of the first and second membranes so that the first membrane has a permeability ratio with respect to the test gas component over the reference gas which ratio is different from that of the second membrane permeability ratio with respect to the test gas component over the reference gas, and
   (c) forming a measuring chamber between the first and second membranes within which the steady state pressure is proportional to the concentration of the component being measured.

2. The method of claim 1 in which there is provided the further step of measuring the steady state pressure in the measuring chamber to indicate the concentration of the test gas component.

3. The method of claim 2 in which step (b) includes forming at least one of said first and second membranes from a polymeric material in which the solubility and diffusivity determine the permeability.

4. The method of claim 2 in which step (b) includes forming at least one of said first and second membranes from a porous material in which the Knudsen diffusion determines the permeability.

5. The method of claim 3 in which step (b) includes forming at least one of said first and second membranes of a polymeric material chosen from the group consisting of dimethyl silicone, ethyl cellulose, silicone-polycarbonate copolymer, trichloropropane, polytetrafluoroethylene, cellulose acetate, polycarbonate, polyethylene, polypropylene, polyurethane, and polyvinylchloride.

6. The method of claim 4 in which step (b) includes forming at least one of said first and second membranes of glass or metal in which the Knudsen diffusion determines the permeability.

7. The method of claims 2, 3 or 4 in which there is provided the further step of forming the first and second membranes of thickness is an effective amount to achieve a steady state pressure in the measuring chamber in a minimum amount of time without overshoot.

8. The method of claims 2, 3 or 4 in which there is provided the further step of selecting the materials of the first and second membranes to provide a response specific to the test gas component.

9. The method of claim 8 in which there is provided the further step of selecting the materials of the first and second membranes to provide the largest possible pressure change in steady state pressure for the smallest change in component concentration.

10. The method of claims 2, 3 or 4 in which there is provided the further step of forming both of the first and second membranes and the measuring chamber of size sufficient to provide a measurement of concentration so that the response is independent of the rate of flow of the test gas and the reference gas over a predetermined range.

11. The method of claims 2, 3 or 4 in which step (c) includes the forming of the measuring chamber into a sealed chamber.

12. The method of claim 11 in which there is provided the further step of providing a test gas flow path and a reference gas flow path for respectively exposing said first membrane to the test gas and the second membrane to the reference gas with the measuring chamber being isolated from both of said gas flow paths.

13. The method of claim 12 in which there is provided the further step of forming a test gas chamber through which is directed the test gas flow and forming a reference gas chamber through which is directed the reference gas flow path and in which the test and reference gas chambers are of small volumes sufficient to minimize mixing volume.

14. A system for measuring the concentration of at least one component of a test gas with respect to a reference gas comprising
first and second gas flow paths respectively for said test gas and said reference gas,
a first semipermeable membrane exposed to said first gas flow path, a second semipermeable membrane exposed to said second gas flow path, said first and second membranes separated from each other to form a measuring chamber isolated from said first and second gas paths, and
the first membrane having a permeability ratio with respect to the test gas component over the reference gas which ratio is different from that of the second membrane permeability ratio with respect to the test gas component over the reference gas whereby the steady state pressure in the measuring chamber is proportional to the concentration of said test gas component being measured.

15. The concentration measuring system of claim 14 in which at least one of said first and second membranes are formed from a polymetric material in which the solubility and diffusivity determine the permeability.

16. The concentration measuring system of claim 14 in which at least one of said first and second membranes are formed from a porous material in which the Knudsen diffusion determines the permeability.

17. The concentration measuring system of claim 15 in which at least one of said first and second membranes is formed of a polymeric material chosen from the group consisting of dimethyl silicone, ethyl cellulose, silicone-polycarbonate, copolymer, trichloropropane, polytetrafluoroethylene, cellulose acetate, polycarboate, polyethylene, polypropylene, polyurethane, and polyvinylchloride.

18. The concentration measuring system of claim 16 in which at least one of the first and second membranes is formed of glass or metal in which the Knudsen diffusion determines the permeability.

19. The concentration measuring system of claims 15 or 16 in which the first and second membranes are of thickness in an effective amount to achieve a steady state pressure in the measuring chamber in a minimum amount of time without overshoot.

20. The concentration mesuring system of claims 15 or 17 in which the first and second membranes are of materials selected to provide a response specific to the test gas component.

21. The concentration measuring system of claim 20 in which the first and second membranes are selected of material to provide the largest possible pressure change in steady state pressure for the smallest change in component concentration.

22. The concentration measuring system of claims 15 or 16 in which the first and second membranes and the measuring chamber are formed of size sufficient to provide a measurement of concentration so that the response is independent of the rate of flow of the test gas and reference gas over a predetermined range.

23. The concentration measuring system of claims 15 or 16 in which said measuring chamber is formed as a sealed chamber.

24. The concentration measuring system of claim 23 in which there is provided a test gas chamber for said first membrane through which is directed the first gas flow path and a reference gas chamber for said second membrane through which is directed the second gas flow path and in which the test and reference gas chambers are of small volume sufficient to minimize mixing volume.

25. The concentration measuring system of claim 24 in which there is provided manometer means fluidly coupled to said sealed measuring chamber to provide a direct readout of the concentration of said test gas component being measured.

26. The concentration measuring system of claim 24 in which there is provided pressure transducer means fluidly coupled to said sealed measuring chamber to provide an electrical signal proportional to the concentration of said test gas component being measured.

27. The concentration measuring system of claim 26 in which there is provided means for converting said electrical signal to a visual display indicating the concentration of said test gas component being measured.

28. The concentration measuring system of claim 24 in which there is provided porous stainless steel supports for said first and second membranes of size sufficient to reduce the volume of said test gas chamber and said reference gas chamber for minimizing mixing volume.

* * * * *